United States Patent
Larré

(10) Patent No.: US 6,461,336 B1
(45) Date of Patent: Oct. 8, 2002

(54) CARDIOLOGICAL MEDICAL EQUIPMENT

(76) Inventor: Jorge Casado Larré, Ave Los Próceres Urbanización Las Flores Merida, Merida (VE)

(*) Notice: Subject to any disclaimer, the term of this patent is extended or adjusted under 35 U.S.C. 154(b) by 0 days.

(21) Appl. No.: 09/500,291

(22) Filed: Feb. 8, 2000

(51) Int. Cl.⁷ .................................................. A61M 5/00
(52) U.S. Cl. .................. 604/264; 604/284; 604/523; 604/532
(58) Field of Search .................... 604/264, 284, 604/500, 507, 508, 510, 523, 528, 532, 534, 535; 606/194

(56) References Cited

U.S. PATENT DOCUMENTS

| | | | | |
|---|---|---|---|---|
| 5,385,562 | * | 1/1995 | Adams | 604/528 |
| 5,669,924 | | 9/1997 | Shaknovich | 606/108 |
| 5,695,457 | * | 12/1997 | St. Goar et al. | 604/532 X |
| 5,720,735 | * | 2/1998 | Dorros | 604/284 |
| 5,810,790 | * | 9/1998 | Ebling et al. | 604/523 |
| 5,976,103 | * | 11/1999 | Martin | 604/284 X |

* cited by examiner

*Primary Examiner*—John D. Yasko
(74) *Attorney, Agent, or Firm*—J. Sanchelima

(57) ABSTRACT

An angioplastic device used for treating the areas surrounding bifurcated vessels. The device has an elongated and relatively flexible tubular guiding catheter assembly that slidably houses a guide positioning assembly therein. The elongated tubular guiding catheter assembly has a non-circular lumen that cooperatively receives a guides carrier assembly with a non-circular cross-section. The guide carrier assembly includes two internal through passages through which two guide members are slidably passed and directed to different branches in a bifurcated vessel. The guide members carry at the distal end a balloon with or without stents to be positioned against the internal walls of the vessels being treated.

3 Claims, 4 Drawing Sheets

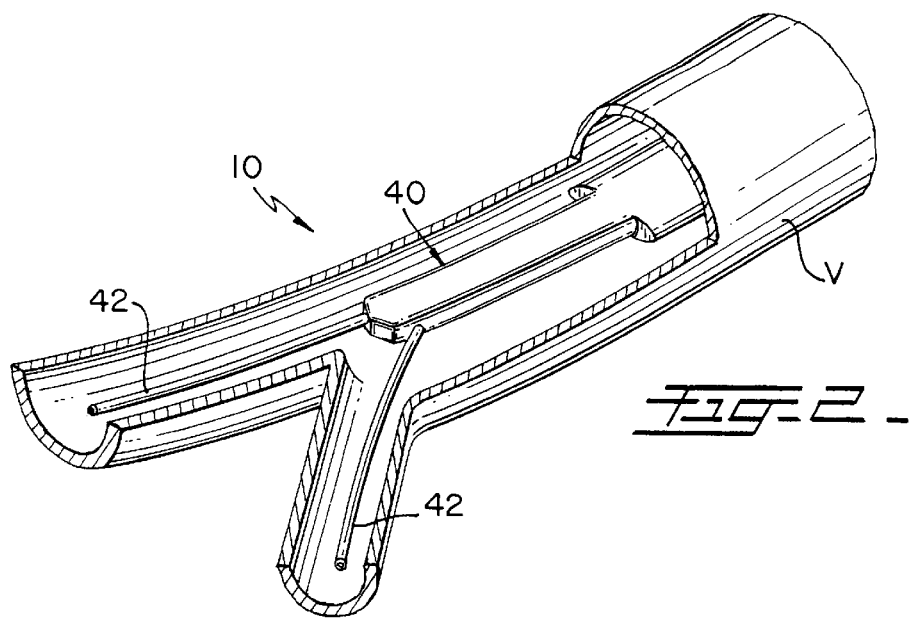
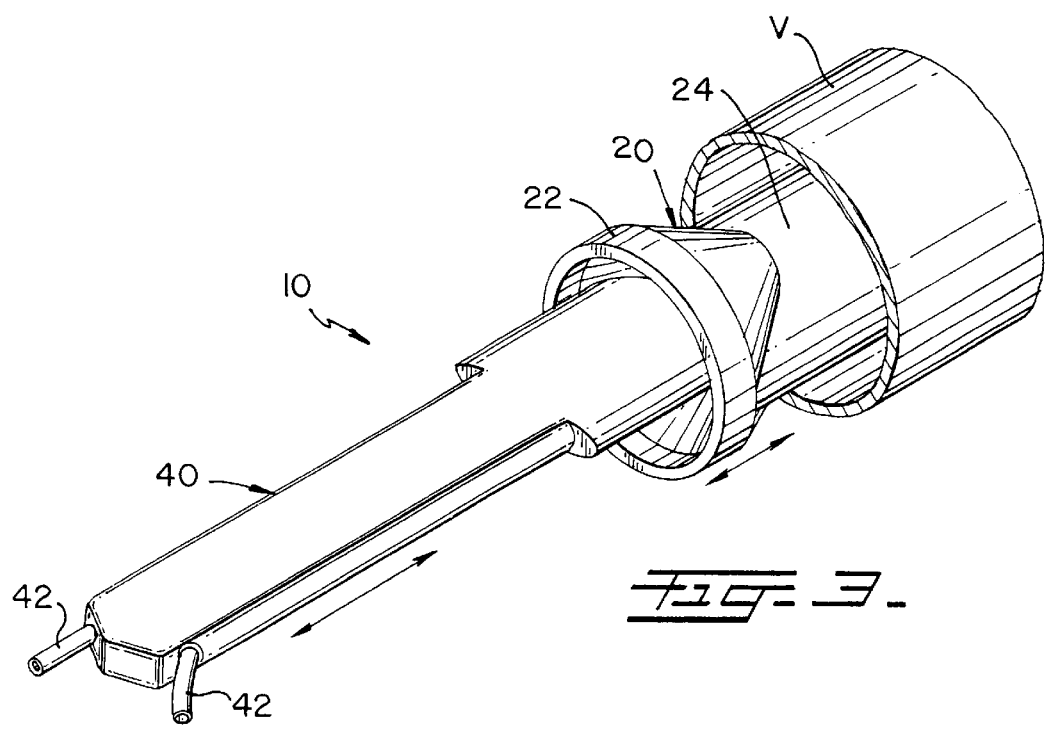

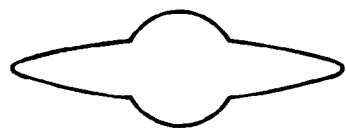
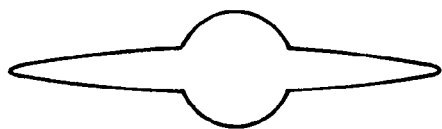
_Fig-6_

CARDIOLOGICAL MEDICAL EQUIPMENT

BACKGROUND OF THE INVENTION

1. Field of the Invention.

The present invention relates to a vascular device, and more particularly, to such a device that is particularly useful for treating of stenotic lesions located at the bifurcation of veins and arteries.

2. Description of the Related Art.

Several designs for angioplastic and vascular devices have been designed in the past. However, these prior arts have a distinct and very common problem: The system rotates and it is difficult to maintain control over it. The present invention solves all problems by using catheters with non-circular lumens and cross-sections. The present invention solves this problem by using catheters with non-circular lumens and cross-sections.

Applicant believes that the closest reference corresponds to U.S. Pat. No. 5,669,924 issued to Shaknovich on Sep. 23, 1997 for Y-Shuttle Stent Assembly for Bifurcating Vessels and Method of Using the Same. However, it differs from the present invention because it includes guiding catheter 14 with a circular lumen that allows Y-shuttle to rotate. Also, inherent in the Y-shaped deployment segment is the need to have a relatively large lumen increasing the trauma to the inner walls of the vessels.

Other patents describing the closest subject matter provide for a number of more or less complicated features that fail to solve the problem in an efficient and economical way. None of these patents suggest the novel features of the present invention.

SUMMARY OF THE INVENTION

It is one of the main objects of the present invention to provide a vascular device that includes two guide assemblies retractable and extendable within an elongated holder.

It is another object of this invention to provide a vascular device that includes two catheters over which a user has control over their rotational position.

It is still another object of the present invention to provide a volumetrically efficient device for delivering angioplastic components to remote locations in bifurcated vessels.

It is yet another object of this invention to provide such a device that is inexpensive to manufacture and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which:

FIG. 2 is an isometric representation of the guides carrier assembly positioned within a bifurcated vessel.

FIG. 3 is an isometric representation of the guiding catheter assembly within a vessel.

FIG. 6 is a representation of some of the non-circular cross sections for guides carrier assembly.

DETAILED DESCRIPTION OF THE PREFERRED EMBODIMENT

Figure 1:
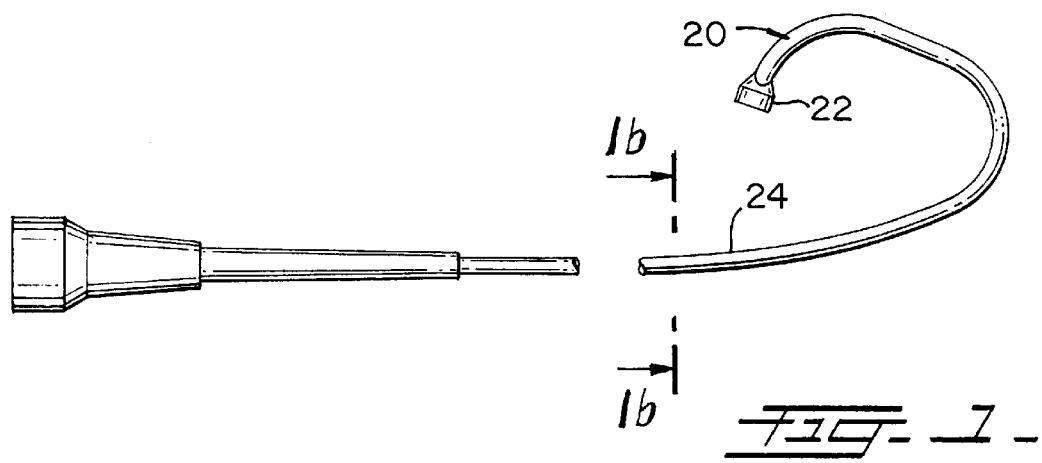
FIG. 1 represents a broken side elevational view of the guiding catheter assembly.

Referring now to the drawings, where the present invention is generally referred to with numeral 10, it can be observed that it basically includes guiding catheter assembly 20, and guides carrier assembly 40. Additionally, and depending on the work being undertaken, other devices are used, including, balloons and stents.

Figure 1A:
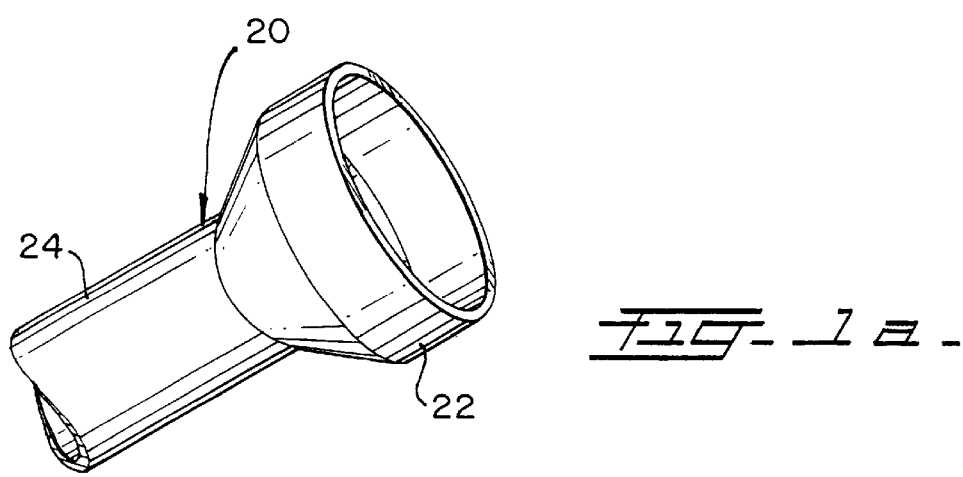
FIG. 1a is an isometric representation of the distal end of the guiding catheter assembly with a trumpet termination.
Figure 1B:
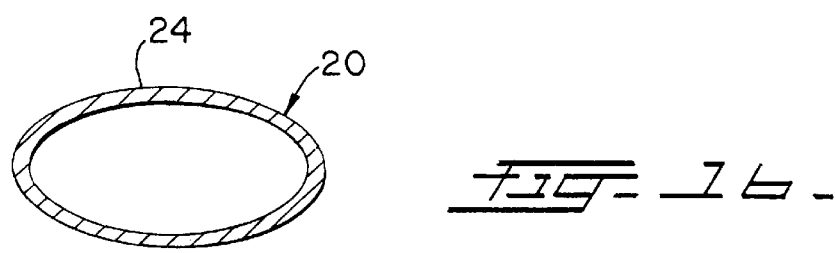
FIG. 1b is a cross-sectional view of the guiding catheter assembly shown in FIG. 1 wherein its lumen is non-circular.
Figure 4:
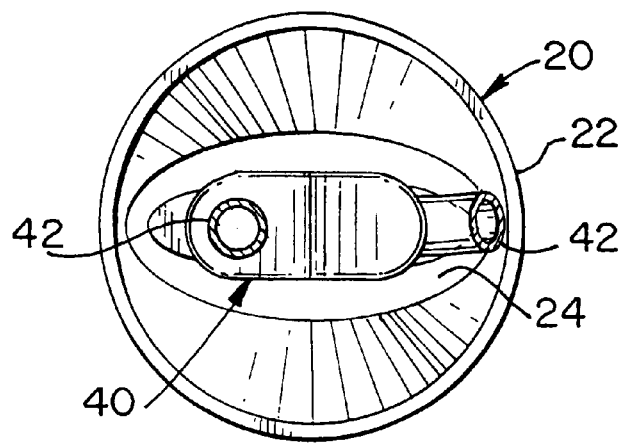
FIG. 4 shows a front view of the guiding catheter assembly within a vessel.
Figure 5:
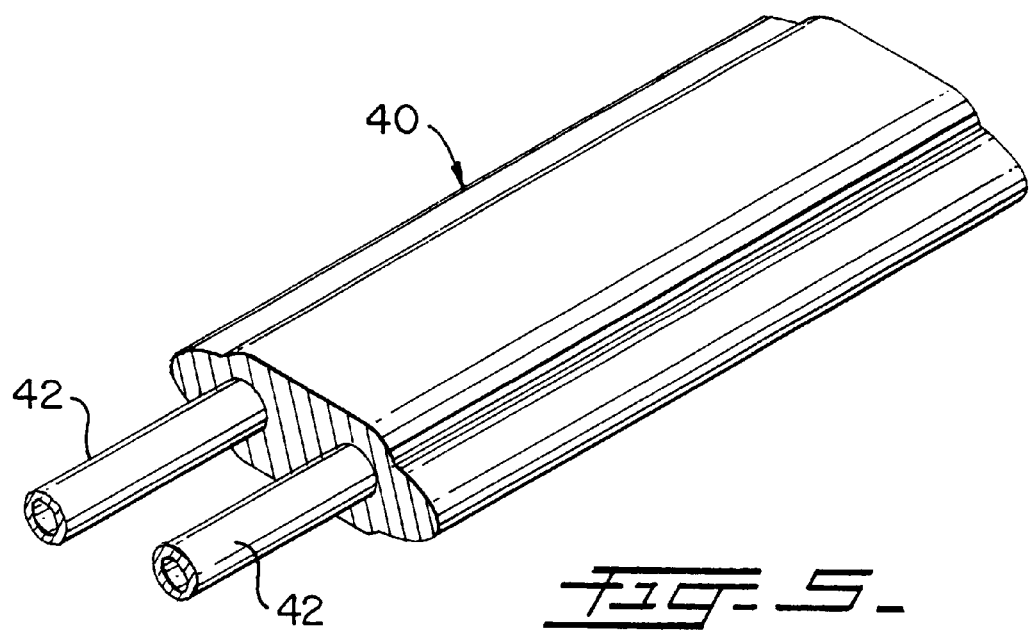
FIG. 5 represents an isometric view of the guides carrier assembly's body.

As shown in FIG. 1 guiding catheter assembly 20 is an elongated tube with a non-circular lumen, as shown in FIG. 1b, and some flexibility to permit its introduction through blood vessels V. Suitable materials are known in the industry to provide minimum friction as assembly 20 advances inside a vessel. As best seen in FIG. 1a the distal end of assembly 20 includes a trumpet-like termination 22 to facilitate the recuperation of stents 80, when necessary. The stents that cannot be successfully installed have been stretched to a larger diameter and without the trumpet-like termination 22 the retrieval is very difficult. The trumpet-like termination 22 guides the unused stents 80 towards the inner tubular cavity 24 of assembly 20 when it is being retrieved.

As represented in FIGS. 2; 3; 4 and 5, guides carrier assembly 40 has a non-circular cross-section that cooperates with the non-circular lumen of assembly 20 to provide the necessary control to the user. The unintended or accidental rotation of guides 42 is avoided. This is specially critical near bifurcated vessels, as shown in FIG. 3. Time is important and currently used devices require pulling out the entire assembly when the guides rotate and land in the wrong positions.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. An angioplastic device comprising:
   A) an elongated tubular guiding catheter assembly having first and second ends, and said elongated tubular guiding catheter assembly including a non-circular lumen;
   B) a guides carrier assembly with third and fourth ends, and having a non-circular cross-section with cooperative dimensions to be slidably housed within said elongated tubular guiding catheter assembly, said carrier assembly including first and second internal through passages; and
   C) two guide members slidably housed within said passages.

2. The device set forth in claim 1 wherein said first end has a trumpet-like termination.

3. The device set forth in claim 2 wherein said first internal through passage extends axially within said guides carrier assembly ending a said third end and said second internal through passage also extending axially within said guides carrier assembly and parallel to said first internal through passage except next to said third end where said second internal through passage extends at a predetermined angle with respect to said first internal through passage.

* * * * *